United States Patent [19]

Cimino et al.

[11] Patent Number: 5,372,929
[45] Date of Patent: Dec. 13, 1994

[54] METHODS FOR MEASURING THE INACTIVATION OF PATHOGENS

[76] Inventors: George D. Cimino, 4839 Full Moon Dr., Richmond, Calif. 94803; Lily Lin, 80 Hill Rd., Berkeley, Calif. 94708

[21] Appl. No.: 825,959

[22] Filed: Jan. 27, 1992

[51] Int. Cl.$^5$ .......................... C12Q 1/68; C12Q 1/70; C12P 19/34
[52] U.S. Cl. .......................................... 435/6; 435/5; 435/91.2; 435/173.1; 436/501; 935/77; 935/78
[58] Field of Search .................... 435/91, 6, 173, 91.2, 435/5, 173.1; 436/63

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,196,281 | 4/1980 | Hearst et al. | 536/28 |
| 4,312,883 | 1/1982 | Baccichetti et al. | 424/279 |
| 4,683,195 | 7/1987 | Mullis et al. | 435/6 |
| 4,683,202 | 7/1987 | Mullis et al. | 435/91 |
| 4,727,027 | 2/1988 | Wiesehahn et al. | 435/173 |
| 4,748,120 | 5/1988 | Wiesehahn | 435/173 |
| 5,221,608 | 6/1993 | Cimino et al. | 435/6 |
| 5,288,605 | 2/1994 | Lin et al. | 435/902 |

OTHER PUBLICATIONS

Cimino et al. (1991, Jan. 11) Nucleic Acids Research, vol. 19 (1), pp. 99–107.
Lin et al. (1984) Blood 74:517–525.
Isaac et al. (1991) Nucleic Acids Res. 19:109–116.
R. Y. Dodd, In: *Transfusion Medicine in the 1990's* (American Assoc. Blood Banks 1990) (S. J. Nance, ed.).
G. D. Cimino, et al., Ann. Rev. Biochem. 54:1151 (1985).
Hearst, et al., Quart. Rev. Biophys. 17:1 (1984).
S. T. Isaacs, et al., Biochemistry 16:1058 (1977).
S. T. Isaacs, et al., Trends in Photobiology (Plenum) pp. 279–294 (1982).
J. Tessman, et al., Biochem. 24:1669 (1985).
H. J. Alter, et al., The Lancet (ii:1446) (1988).
L. Lin, et al., Blood 74:517 (1989).
Hanson, C. V., et al., J. Clin. Microbiol. 23:2030 (1990).
Innis, M. A. et al., eds. *Protocols: A Guide to Methods and Applications*, pp. 261–271 (1990).
Kocher, et al., Proc. Natl. Acad. Sci. USA 86:6196 (1989).
Larzul, D., et al., J., Molecular and Cellular Probes 3:45 (1989).
Lin, L., et al., Blood 78:247a (1991).

*Primary Examiner*—Margaret Parr
*Assistant Examiner*—Carla Myers
*Attorney, Agent, or Firm*—Peter G. Carroll; Kathryn P. Wilke

[57] ABSTRACT

Methods for measuring pathogen inactivation, and in particular, methods for measuring pathogen inactivation in blood and blood products after photochemical decontamination. The methods involve measuring the inhibition of template-dependent enzymatic synthesis of nucleic acid following the addition of compounds that add covalently to nucleic acid.

14 Claims, 6 Drawing Sheets

METHODS FOR MEASURING THE INACTIVATION OF PATHOGENS

FIELD OF THE INVENTION

The present invention relates to new methods for measuring the inactivation of pathogens, and in particular, new methods for measuring pathogen inactivation in blood and blood products after a decontamination process.

BACKGROUND

The safety of the blood supply continues to be threatened by the transmission of pathogens by transfusion. While the threat posed by the human immunodeficiency virus (HIV) and the Acquired Immune Deficiency Syndrome (AIDS) is now widely publicized, contamination of blood products with a number of other blood-borne infectious viral agents is of even greater concern. See R. Y. Dodd, In: *Transfusion Medicine in the 1990's* (American Assoc. Blood Banks 1990) (S. J. Nance, ed.). For example, in the United States, it is estimated that five to ten percent of multiply transfused recipients develop hepatitis accounting for many thousands of cases annually.

The safety of the blood supply cannot be assured by merely testing the blood for pathogens before transfusion. Most testing relies on the detection of antibodies to the pathogen in the prospective blood donor. It is now well-documented that infectious agents can be transmitted by "seronegative" blood donors, i.e., donors that have no detectable antibodies to the pathogen. For example, thirteen cases of transfusion-related AIDS have been reported to the Centers for Disease Control (CDC) among recipients of blood that was pretested and found negative for antibody to the HIV-1 virus.

Most importantly, routine serologic testing will not detect new infectious agents. Each time a new infectious agent is identified, a new test must be designed, developed and approved. During this time, transfusion recipients are at risk. The most dramatic example of this is found in hemophiliac patients receiving repeated exposure to plasma or clotting factor concentrates. While a test for the HIV virus was being developed, this patient population was exposed to untested blood products. As a result, greater than ninety percent of this population now have serologic evidence of past hepatitis or HIV infection, and many have developed overt hepatitis or AIDS.

An alternative approach to eliminate transmission of diseases through blood products is to develop a means to inactivate pathogens in transfusion products. Several methods have been reported to be effective in inactivating or eliminating viral agents, HIV in particular, in human plasma and its derivatives. These methods include thermal inactivation, γ irradiation, laser-UV irradiation, UV irradiation in the presence of β-propiolactone, use of organic solvent and detergent combinations and laser-visible light irradiation in the presence of hematoporphyrin. Unfortunately, most of these methods harm the blood cellular components as well.

A more encouraging approach to blood decontamination is the photochemical decontamination (PCD) process using psoralens. Psoralens are tricyclic compounds formed by the linear fusion of a furan ring with a coumarin. Psoralens can intercalate between the base pairs of double-stranded nucleic acids, forming covalent adducts to pyrimidine bases upon absorption of long-wave ultraviolet light (UVA). G. D. Cimino et al., Ann. Rev. Biochem. 54:1151 (1985). Hearst Et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977). S. T. Isaacs et al., Trends in Photobiology (Plenum) pp. 279–294 (1982). J. Tessman et al., Biochem. 24:1669 (1985). Hearst et al., U.S. Pat. Nos. 4,124,589, 4,169,204, and 4,196,281, hereby incorporated by reference.

The PCD process has been shown to inactivate a wide range of pathogens in some blood products. See H. J. Alter et al., The Lancet. (ii:1446) (1988). L. Lin et al., Blood 74:517 (1989). G. P. Wiesehahn et al., U.S. Pat. Nos. 4,727,027 and 4,748,120, hereby incorporated by reference, describe the use of PCD process utilizing a combination of 8-methoxypsoralen (S-MOP) and irradiation. They show that the PCD process can effectively inactivate a number of pathogens, including intracellular HIV. Furthermore, the harm to the blood product that would otherwise occur in the PCD process because of energy transfer, was specifically suppressed by limiting the concentration of molecular oxygen.

What remains unclear about the PCD process is the efficiency of inactivation of free viral and provital genetic material, particularly with RNA viruses. Because of the low sensitivity and time consuming nature of current biological culture methods, there is no adequate assay at present for measuring pathogen inactivation in blood products.

SUMMARY OF THE INVENTION

The present invention relates to new methods for measuring pathogen inactivation, and in particular, new methods for measuring pathogen inactivation in blood and blood products after a decontamination process. The methods involve measuring the inhibition of template-dependent enzymatic synthesis of nucleic acid following the addition of compounds that add covalently to nucleic acid, i.e., "addition compounds". In one embodiment, the addition compounds are selected from the group comprising photoreactive compounds. In a preferred embodiment, the photoreactive compound is selected from the group comprising isopsoralens and psoralens.

In one embodiment, the present invention provides a method for measuring the inactivation of pathogens in blood products, comprising the sequential steps: a) providing, in any order, i) blood product comprising nucleic acid-containing blood cells and blood cells having no nucleic acid, ii) blood product containing means, iii) at least one addition compound, iv) amplification reagents, v) at least one amplification enzyme, vi) a first and a second primer set and vii) a first and a second amplification reaction containing means; b) adding to the blood product in the blood product containing means an addition compound to create a mixture; c) treating the mixture so that the addition compound adds to the nucleic acid of the nucleic-acid containing blood cells; d) preparing the blood product such that the nucleic acid from the nucleic acid-containing blood cells is amplifiable; e) adding to the first amplification reaction containing means, in any order, a portion of the amplifiable nucleic acid, the amplification reagents, the amplification enzyme, and the first primer set, to create a reaction mixture; f) adding to the second amplification reaction containing means, in any order, a portion of the amplifiable nucleic acid, the amplification reagents, the amplification enzyme, and the second primer set, to create a reaction mixture; and g) exposing each of the first and second amplification reaction containing means to conditions sufficient to provide amplification products of different lengths.

In one embodiment the blood product comprises platelets and the nucleic acid-containing blood cells are lymphocytes.

In one embodiment, amplification is carried out using the polymerase chain reaction and a plurality of primer sets so as to provide PCR products of different lengths. In one embodiment, the plurality of primer sets are amplified together by PCR. In another embodiment, each primer set is amplified separately by PCR.

In one embodiment employing two different primer sets, the present invention contemplates that the first primer set is capable of generating a product of a length short enough to be essentially transparent to the addition of the addition compounds to the nucleic acid under a defined set of amplification conditions (i.e., regardless of the efficiency of the covalent addition of addition compounds, the length of the product is sufficient such that amplification product will be detected), and the second primer set is capable of generating a product of a length long enough to be affected—not completely inhibited but inhibited in part—by the addition of the addition compounds to the nucleic acid of the nucleic acid-containing blood cells with the same amplification conditions as above (i.e., the efficiency of the covalent addition of addition compounds will be reflected in the amount of amplification product detected).

In another embodiment, the present invention provides a method for measuring the inactivation of pathogens in blood products, comprising the sequential steps: a) providing, in any order, i) blood product comprising nucleic acid-containing blood cells and blood cells having no nucleic acid, ii) blood product containing means, iii) at least one addition compound, iv) amplification reagents, v) at least one amplification enzyme, vi) a first, a second and a third primer set and vii) a first, a second and a third amplification reaction containing means; b) adding to the blood product in the blood product containing means an addition compound to create a mixture; c) treating the mixture so that the addition compound adds to the nucleic acid of the nucleic-acid containing blood cells; d) preparing the blood product such that the nucleic acid from the nucleic acid-containing blood cells is amplifiable; e) adding to the first amplification reaction containing means, in any order, a portion of the amplifiable nucleic acid, the amplification reagents, the amplification enzyme, and the first primer set, to create a reaction mixture; f) adding to the second amplification reaction containing means, in any order, a portion of the amplifiable nucleic acid, the amplification reagents, the amplification enzyme, and the second primer set, to create a reaction mixture; g) adding to the third amplification reaction containing means, in any order, a portion of the amplifiable nucleic acid, the amplification reagents, the amplification enzyme, and the third primer set, to create a reaction mixture; and g) exposing each of the first, second and third amplification reaction containing means to conditions sufficient to provide amplification products of different lengths.

In a preferred embodiment employing three different primer sets, the present invention contemplates that the first primer set is capable of generating a product of a length short enough to be essentially transparent to the addition of the addition compounds to the nucleic acid under a defined set of amplification conditions (i.e., regardless of the efficiency of the covalent addition of addition compounds, the length of the product is sufficient such that amplification product will be detected), the second primer set is capable of generating a product of a length long enough to be affected—not completely inhibited but inhibited in part—by the addition of the addition compounds to the nucleic acid of the nucleic acid-containing blood cells with the same amplification conditions as above (i.e., the efficiency of the covalent addition of addition compounds will be reflected in the amount of amplification product detected), and the third primer set capable of generating a product of a length long enough to be completely inhibited by the addition of addition compounds to the nucleic acid of the nucleic-acid containing blood cells (i.e., covalent addition of the addition compounds will be reflected by the complete absence of measurable amplification product).

DESCRIPTION OF THE INVENTION

Figure 1:
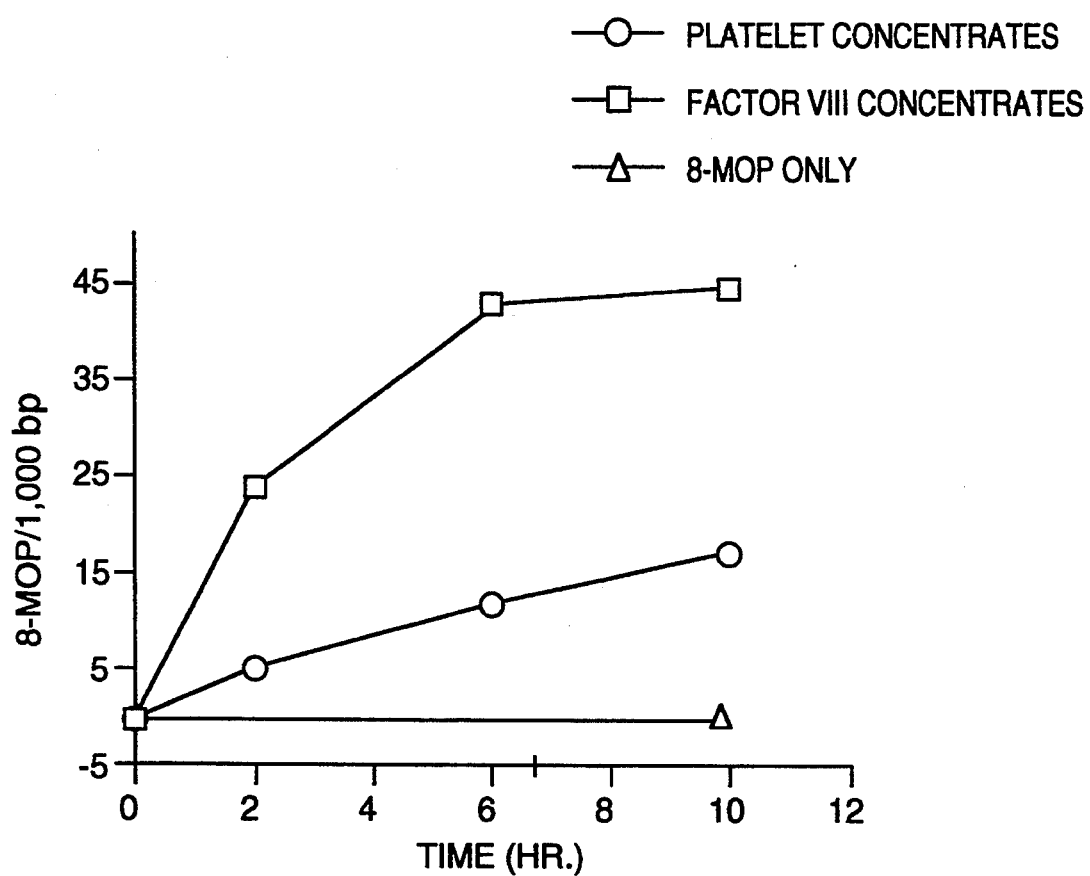
FIG. 1 is a graph showing the photoaddition of 8-methoxypsoralen to normal lymphocyte DNA.

Where decontamination of pathogens is used as a treatment for blood product that will be transfused, it is essential that pathogen inactivation be complete. That is to say, partial inactivation will leave some portion of infectious organisms available to cause disease.

The present invention relates to new methods for measuring pathogen inactivation. In particular, the present invention provides new methods for measuring pathogen inactivation in blood and blood products after decontamination. The methods can be used to obtains a sensitive quantitative measurement of the efficiency of decontamination. The methods, therefore, may be used as a quality control assay to verify adequate treatment of blood product in any given case.

To appreciate that, in any given case, a pathogen inactivation method may or may not achieve complete inactivation, it is useful to consider a specific example.

A bacterial culture is said to be sterilized if an aliquot of the culture, when transferred to a fresh culture plate and permitted to grow, is undetectable after a certain time period. The time period and the growth conditions (e.g., temperature) define an "amplification factor". This amplification factor along with the limitations of the detection method (e.g., visual inspection of the culture plate for the appearance of a bacterial colony) define the sensitivity of the inactivation method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the method appears to be completely effective (and above which the method is, in fact, only partially effective).

This interplay between the amplification factor of an assay and the threshold that the detection method defines, can be illustrated. For example, bacterial cells can be applied to a plate; the detection method is arbitrarily chosen to be visual inspection. Assume the growth conditions and time are such that an overall amplification of $10^6$ has occurred. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the inactivation method will appear effective. Given the amplification factor of $10^4$ and a detection threshold of $10^6$, the sensitivity limit would be 100 bacterial cells; if less than 100 viable bacterial cells were present in the original aliquot of the bacterial culture after the sterilization method is performed, the culture would still appear to be sterilized.

Such a situation is common for bacterial growth assays. The sensitivity of the assay is such that viable bacterial cells are present but the assay is unable to detect them.

The same holds true for virus inactivation. In the past, inactivation of virus is demonstrated by a biological assay such as an enzyme assay (e.g., reduction in reverse transcriptase) or cell culture (e.g., virus-induced host cell death). A more sensitive method has been described by C. V. Hanson et al. for quantifying HIV. See J. Clin. Microbiol. 23:2030 (1990). The method is a plaque assay employing HIV-sensitive cells in a monolayer. A fluorescent stain is used and detection is made by visualization. While the sensitivity of the assay is much improved over other methods, some small amount of viable virus may be present even when the assay is negative. Indeed, it has been found that this approach to measuring viral inactivation typically cannot distinguish the situation where inactivation of the virus is complete from the situation where inactivation is not complete.

Rather than measuring pathogen growth to evaluate an inactivation process, the methods of the present invention involve measuring the inhibition of template-dependent enzymatic synthesis of nucleic acid following the addition of compounds that add covalently to nucleic acid. Enzymatic synthesis that involves nucleic acid, either solely as a template (e.g., translation involves the use of nucleic acid as a template to make polypeptides) or as both a template and a product (replication and transcription use nucleic acid as a template to produce nucleic acid) is hereinafter referred to as "template-dependent enzymatic synthesis."

In the case of replication, nucleic acid polymerases replicate a nucleic acid molecule ("template") to yield a complementary ("daughter") nucleic acid molecule. For example, DNA polymerase I, isolated from *E. Coli*, catalyzes the addition of deoxyribonucleoside triphosphates to the 3' end of a short segment of DNA ("primer") hybridized to a template strand to yield a daughter of the template, starting from a mixture of nucleotides (dATP, dGTP, dCTP, and dTTP). This 5' to 3' template-dependent enzymatic synthesis is also called "primer extension." The reaction will not take place in the absence of template. The reaction can be measured if one or more of the nucleotides are labelled (usually they are radiolabelled with $^{32}P$.

While amplification of pathogen nucleic acid is possible, it should be kept in mind that blood is subjected to decontamination on whether a pathogen is present or not. Thus, when pathogen is not present, attempts to amplify pathogen nucleic acid would result in no amplification product. Secondly, the reagents for amplification of pathogen nucleic acid are typically specific for that pathogen; one would need a comprehensive method to reflect pathogen diversity. For these reasons, the preferred approach of the present invention is to amplify nucleic acid that is present in nucleic acid-containing cells of the blood product rather than nucleic acid of the pathogen. This approach is generic; it does not rely on the specific characteristics of each and every possible pathogen.

Normally, the amount of existing nucleic acid-containing cells in the blood product as a result of blood processing is sufficient. However, the present invention also contemplates an embodiment involving seeding the blood product with nucleic acid for this purpose. In any event, the present invention contemplates that the nucleic acid may be genomic or mitochondrial DNA. Furthermore, this nucleic acid can be cellular RNA.

In one embodiment, the present invention provides a method for determining the efficiency of a decontamination technique (such as the PCD process) to inactivate virus in blood products (e.g., platelet concentrates), comprising measuring the ability of the inactivation process to inhibit replication of intracellular nucleic acid as measured by a nucleic acid amplification assay. In one embodiment, the amplification assay is the highly sensitive polymerase chain reaction (PCR).

PCR is a method for increasing the concentration of a segment of a target sequence in a mixture of genomic DNA without cloning or purification. See K. B. Mullis et al., U.S. Pat. Nos. 4,683,195 and 4,683,202, hereby incorporated by reference. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process the method is referred to by the inventors as the "Polymerase Chain Reaction". Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labelled probe; incorporation of biotinylated primers followed by avidin-enzyme conjugate detection; incorporation of $^{32}P$ labelled deoxynucleotide triphosphates, e.g., dCTP or dATP, into the amplified sergeants). In addition to genomic DNA, any oligonucleotide sequence can be amplified with the appropriate set of primer molecules.

The PCR amplification process is known to reach a plateau concentration of specific target sequences of approximately $10^{-8}M$. A typical reaction volume is 100 μl, which corresponds to a yield of $6 \times 10^{11}$ double stranded product molecules.

"Amplification reagents" are defined as those reagents (deoxyribonucleoside triphosphates, buffers, etc.) needed for amplification except for nucleic acid, primers, and the amplification enzyme. In one embodiment, an amplification reaction containing means is a reaction vessel (test tube, microwell, etc.).

PCR is a polynucleotide amplification protocol. The amplification factor that is observed is related to the number (n) of cycles of PCR that have occurred and the efficiency of replication at each cycle (E), which in turn is a function of the priming and extension efficiencies during each cycle. Amplification has been observed to follow the form $E^n$, until high concentrations of PCR product are made. At these high concentrations (approximately $10^{-8}$ M/l) the efficiency of replication falls off drastically. This is probably due to the displacement of the short oligonucleotide primers by the longer complementary strands of PCR product. At concentrations in excess of $10^{-8}M$, the rate of the two complementary PCR amplified product strands finding each other during the priming reactions become sufficiently fast that this occurs before or concomitant with the extension step of the PCR procedure. This ultimately leads to a reduced priming efficiency, and therefore, a reduced cycle efficiency. Continued cycles of PCR lead to declining increases of PCR product molecules. PCR product eventually reaches a plateau concentration.

While not limited to any particular theory, the present invention contemplates that, when a psoralen adduct is present on nucleic acid within the segment of the target sequence bounded by the primer sequences, the extension step of the PCR process will result in a truncated extension product that is incapable of being replicated in subsequent cycles of the PCR process.

Importantly, the inactivation will be incomplete if some of the pathogens escape modification by the decontamination process. This process is, by its nature, a statistical process. This process can be characterized by measuring an average number (a) of adducts per DNA strand. Not all of the strands will have a adducts per strand. If the addition reaction is governed by Poisson statistics, the fraction of molecules that contain n modifications in a large population of molecules that have an average of a modifications is given by $f_a(n)$ (see Table 1). A fraction of molecules, $f_a(O)$, will contain no modifications and are therefore considered non-sterilized, that is, "$f_a(O)$" represents the fraction of strands with zero adducts when the average number of adducts per strand is a and "$Nf_a(O)$" represents the number of unmodified molecules, calculated for a total of $10^6$ molecules ($N=10^6$).

Table 1 evaluates the unmodified fraction of DNA strands that are expected if an average of a modifications per strand exists. Although the

TABLE 1

$$f_a(n) = [a^n e^{-a}]/n!$$
$$N = 10^6, f_a(0) = e^{-a}$$

| a | $f_a(0)$ | $Nf_a(0)$ |
|---|---|---|
| 3 | 0.050 | $5.0 \times 10^4$ |
| 4 | 0.018 | $1.8 \times 10^4$ |
| 5 | 0.007 | $6.7 \times 10^3$ |
| 6 | 0.0025 | $2.5 \times 10^3$ |
| 7 | 0.0009 | $9.1 \times 10^2$ |
| 8 | 0.0003 | $3.3 \times 10^2$ |
| 9 | 0.00012 | $1.2 \times 10^2$ |
| 10 | 0.000045 | $4.5 \times 10^1$ |
| 11 | 0.000017 | 17.0 |
| 12 | 0.0000061 | 6.1 |
| 13 | 0.0000023 | 2.2 |
| 14 | 0.00000083 | .8 |
| 15 | 0.00000030 | .3 |
| 16 | 0.00000011 | .1 |
| 17 | 0.00000004 | 0.04 | fraction of molecules with no modifications is small for all values of a, the expected number of unmodified molecules is large when the PCD process is applied to a large number of molecules (N). For example, Table 1 shows that $2.5 = 10^3$ unmodified molecules are expected if there is an average of 6 effective adducts per strand in a population of $10^6$ strands. Effective adducts are those adducts that occur in the segment of a target molecule that is bounded by the primer sequences. Where photoreactive compounds are employed, alterations of the modification density can be expected through the use of different photoreactive compounds, or the use of the same photoreactive compound at different concentrations. In particular, the modification density is expected to increase through the use of the same photochemical agent at higher concentrations or the use of longer irradiation times.

For a fixed modification density the present invention contemplates another method of improving the sensitivity limit for evaluating the PCD process. The important statistical parameter is the average number of adducts per PCR strand. By choosing PCR primers judiciously, the length of the PCR products can be varied, and therefore, the average number of adducts per strand can be varied. The present invention, therefore, contemplates the use of a plurality of primer sets so as to provide PCR products of different lengths.

In one embodiment, the present invention contemplates two different primer sets: the first generating a product of a length short enough to be essentially transparent to the PCD process (i.e., regardless of the efficiency of the covalent addition of photoreactive compounds, PCR product will be detected under a defined set of amplification conditions), and the second generating a product of a length long enough to be affected—but not completely inhibited—by the PCD process (i.e., the efficiency of the covalent addition of photoreactive compounds will be reflected in the amount of PCR product detected).

In a preferred embodiment, the present invention contemplates three different primer sets: the first generating a product of a length short enough to be essentially transparent to the PCD process, the second generating a product of a length long enough to be affected—but not completely inhibited—by the PCD process, and the third generating a product of a length long enough to be completely inhibited by the PCD process (i.e., covalent addition of photoreactive compounds will be reflected by the complete absence of measurable PCR product).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μ(microliters); cm (centimeters); mm (millimeters); μm (micrometers); nm (nanometers); °C. (degrees Centigrade); Ci (Curies); MW (molecular weight); OD (optical density); DMSO (dimethyl sulfoxide); EDTA (ethylenediamine-tetracetic acid); 1xTE (buffer: 10 mM Tris/1 mM EDTA, pH 7.5); 1xTaq (buffer: 50 mM KCl, 2.5 mM $MgCl_2$, 10 mM Tris, pH 8.5, 200 μg/ml gelatin); PAGE (polyacrylamide gel electrophoresis); UV (ultraviolet); V (volts); W (watts); mA (milliamps); bp (base pair); CPM (counts per minute).

In many of the examples below, 8-methoxypsoralen is used. Generally, stock 8-MOP is diluted in DMSO (100 mg/ml) and added to a final concentration of 300 μg/ml.

In some instances below, amplification of human histocompatibility (HLA) Class II genes was performed using primer pair GH26/GH27 and human placental DNA to produce a 242-mer product. The sequences of these primers are:

either 8M urea, containing 0,025% tracking dyes (bromphenol blue and xylene cyanol), or in 80% formamide, 10% glycerol, 0.025% tracking dyes, then electrophoresed for 30-60 minutes at 300 Volts. Following PAGE, individual bands were, in most cases, visualized by autoradiography. Autoradiography involved exposure overnight at −70° C. to Kodak XAR-5 films with an intensifying screen.

In order to visualize with autoradiography, PCR products were internally radiolabelled. This simply involved adding 2 μCi of α-$^{32}$P-dCTP (3000 Ci/mmole, NEN Research Products, Boston Mass., U.S.A.) to each PCR reaction. The internally-radiolabelled PCR products are directly fractionated by this denaturing PAGE.

In some cases, the visualized bands were cut from the gel and collected for scintillation counting. Scintillation counting involved the use of a scintillation fluid and a commercial scintillation counter (Searle Analytic 92, Model #000 006893).

Generally, PCR was carried out using 175-200 μM dNTPs (deoxyribonucleoside 5'-triphosphates) and 0.1 to 1.0 μM primers. 2.5 to 5.0 Units/ 100 μl of Taq polymerase was used. PCR reactions were overlaid with 30-100 μl light mineral oil. A typical PCR cycle for HIV amplification using a Perkin-Elmer Cetus DNA Thermal Cycler (Part No. N8010150) was: denaturation at 95° C. for 30 seconds; annealing at 55° C. for 30 seconds; and extension at 72° C. for 1 minute. PCR cycles were normally carried out in this manner for between 20 to 30 cycles followed by 7 minutes at 72° C. PCR product or "amplicon" was then detected.

In some of the examples below, platelet concentrates are used. Platelets are prepared by differential centrifugation of whole blood collected from random blood donors. The preparation step concentrates the platelets in reduced volumes of plasma ranging from about 50 to 100 ml. The concentrates contain approximately $5.5 \times 10^{10}$ platelets per bag as well as a variable amount ($10^7$ to $10^8$) of contaminating lymphocytes.

Unless otherwise indicated, the UVA irradiation device consists of two banks of Sylvania Dermacontrol lamps (one above, and one below, the sample) capable of producing approximately 20 mW/cm of light be-

| GH26 | 5'-GTGCTGCAGGTGTAAACTTGTACCAG-3' | (Seq. Id. No. 1) |
| GH27 | 5'-CACGGATCCGGTAGCAGCGGTAGAGTTG-3' | (Seq. Id. No. 2) |

These primers and other primers are described in *PCR Protocols: A Guide To Methods and Applications*, Innis, M. A. et al. eds., pp. 261-271 (1990)).

In another case, amplification of human globin sequences was performed using primer pair KM38/RS118 to produce a 135-mer product and RS40/RS80 to produce a 989-met product. The sequences of these primers are:

tween 320-400 nm. The approximate irradiation path length of the platelet mixture in the irradiation chamber was 0.5 cm.

EXAMPLE 1

In this experiment, the amount of 8-MOP bound to normal lymphocytes seeded into platelets and Factor VIII concentrates was measured. As starting material,

| KM-38 | 5'-TGGTCTCCTTAAACCTGTCTTG-3' | (Seq. Id. No. 3) |
| RS-118 | 5'-ACACCATGGTGCACCTGACT-3' | (Seq. Id. No. 4) |
| RS-40 | 5'-ATTTTCCCACCCTTAGGCTG-3' | (Seq. Id. No. 5) |
| RS-80 | 5'-TGGTAGCTGGATTGTAGCTC-3' | (Seq. Id. No. 6) |

Denaturing (8M urea) polyacrylamide mini-gels were used. 10 to 12.5% gels were used for oligonucleotides between 40 and 400 base pairs in length; 6 to 8% gels were used for longer sequences. Depending on the length of DNA to be analyzed, samples were loaded in $0.8 \times 10^8$ lymphocytes were seeded into a unit of platelet concentrates or 10 ml of clotting Factor VIII concentrates. 8-MOP was added to a final concentration of 300 ug/ml. $^3$H-8-MOP was added to a specific activity of 4.73 uCi/mg. The platelets were irradiated in their storage bag (PL 732, Fenwal, Baxter). The Factor VIII concentrate was irradiated in a petri dish. The samples were irradiated from above and below by GE type F20T12-BLB fluorescent UVA (320–400 nm) bulbs with an electric fan blowing gently across the lights to cool the area. The temperature was maintained between 22° and 27° C. during irradiation. The platelet irradiation was carried out in an atmosphere of 5% $CO_2$ and 95% $N_2$. Available UVA light was measured (by a Black-ray longwave UV meter) with both light banks turned on. The total measured light intensity was 3.5–4.8 mW/cm$^2$. The Factor VIII concentrate irradiation was carried out with no $O_2$ control. Control samples included one which received no treatment and one to which only 8-MOP was added and no UVA light was applied.

Following irradiation, total cellular lymphocyte DNA was extracted by phenol extraction following proteinase K digestion. The DNA was then ethanol precipitated three times. The number of 8-MOP molecules covalently bound per 1,000 base pair was determined by measuring the quantity of DNA ($A_{260}$ nm) using a spectrophotometer and the $^3$H-CPM associated with the DNA using a scintillation counter. FIG. 1 shows that 8-MOP adduct formation is a function of UVA irradiation time. Treatment with 8-MOP alone without UVA light for up to 10 hours resulted in no 8-MOP addition to cellular DNA. For UVA irradiated platelet concentrates, the number of 8-MOP adducts increased with time to a level of 17.2 adducts/1,000 bp. For Factor VIII concentrates, 8-MOP adducts reached a level of 43.5/1,000 bp after 6 hours of UVA irradiation.

EXAMPLE 2

In this experiment, the ability of PCD treatment to inhibit replication of a small segment of cellular DNA was determined. The nucleic acid from Example 1 was processed using the PCR reaction to determine if a small segment of cellular DNA could be replicated. Lymphocyte DNA (1 ug of total DNA) was utilized as the template with the human HLA primers, GH26 and GH27 (Cetus Corp., Emeryville, Calif.). In these experiments the PCR reaction was run for 20 cycles. The PCR products were analyzed by electrophoresis on a 12% denaturing polyacrylamide gel and autoradiography (FIG. 2).

The predominant PCR product of untreated lymphocyte DNA using these primers (FIG. 2, lane 6) is a 242 bp fragment in the HLA-DQA locus. The presence of 10 $\mu$g/ml 8-MOP (FIG. 2, lane 7) or 2% DMSO (FIG. 2, lane 8) did not inhibit the PCR reactions. A similar amount of the 242 bp fragment was detected using lymphocyte DNA treated with 8-MOP without UVA (FIG. 2, lane 1).

Figure 2:
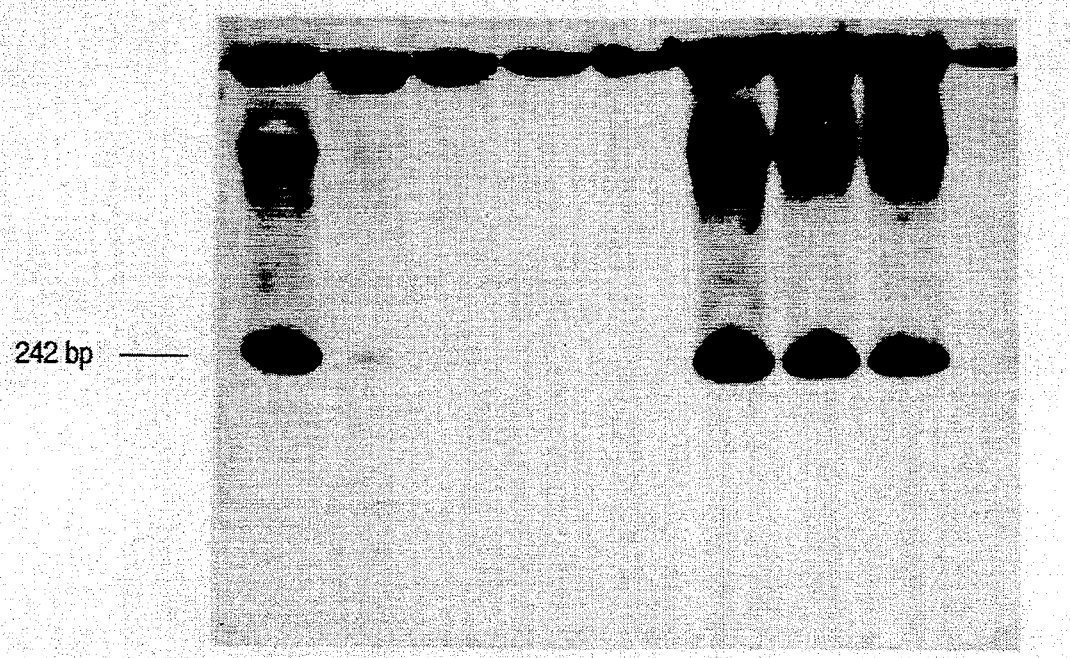
FIG. 2 is a photograph of an autoradiograph of electrophoresed, PCR-amplified, internally-radiolabelled, HLA sequences following photochemical decontamination of platelet concentrates containing normal lymphocytes.

In contrast, PCR mediated replication of this DNA segment was markedly inhibited when PCD treated lymphocyte DNA was used as the template (FIG. 2, lanes 2–5). The degree of inhibition appears to be a function of the number of 8-MOP adducts within each template. Only a small amount of the 242 bp fragment was detected if 8-MOP adducts were present at an average of 5.6 per 1,000 bp (FIG. 2, lane 2), none of the 242 bp fragment was visible in samples where 8-MOP adducts were present at levels greater than 12 per 1,000 bp (FIG. 2, lanes 3, 4 and 5). Thus, at levels of 8-MOP addition achievable in lymphocytes contaminating blood products, PCR mediated replication of a very small DNA segment appears to be strongly inhibited. This 242 bp DNA segment codes for 80 amino acids which is far smaller than any potentially infectious provital DNA segment. Furthermore, the reagents used in the PCD technique do not interfere with the PCR assay system. This experiment indicates that psoralen adducts block replication of genomic DNA of lymphocytes in blood products. It also is highly suggestive that this method will be effective against intranuclear proviral DNA.

EXAMPLE 3

Example 1 demonstrated 8-MOP photoaddition to normal lymphocyte DNA in platelet concentrates and Example 2 showed that this modification could be detected by PCR, consistent with data published earlier (poster presentation at the 31st annual meeting of The American Society of Hematology, 1989). In this example, the photoaddition kinetics of 8-MOP to cellular DNA of H9 cells added to platelet concentrates are established.

Uninfected (2.5×10$^7$) H9 cells in one ml of Dulbecco's modified Eagle's minimum essential medium (DMEM)/15% fetal bovine serum (FBS) were added to one unit of platelet concentrate. Stock 8-MOP (100 mg/ml in DMSO) was added to a final concentration of 300 $\mu$g/ml. $^3$H-8-MOP was added to a specific activity of 118 mCi/mmole. 5 ml of the mixture was transferred to a siliconized glass chamber equipped with an outer jacket in which $H_2O$ was circulated to maintain the temperature at 25° C. The gas phase above the platelet suspension was flushed with 95% $N_2$/5% $Co_2$ for 30 minutes in order to reduce the concentration of $O_2$ in the platelet concentrate and then tightly capped before placing in the Dermacontrol irradiation device (described above). Individual samples in separate chambers were set up for each UVA irradiation time point. The control samples included an untreated sample and a sample to which only 8-MOP was added.

H9 cells were recovered from the platelet concentrate by centrifugation. The total DNA was purified using the standard phenol/chloroform extraction procedure following proteinase K digestion. The DNA content was determined spectrophotometrically after 2 and 3 ethanol precipitations. The $^3$H-8-MOP content in the same sample used for the spectrophotometric measurement was determined by liquid scintillation counting. The level of DNA photomodification was calculated from the specific activity of the added $^3$H-8-MOP.

Figure 3:
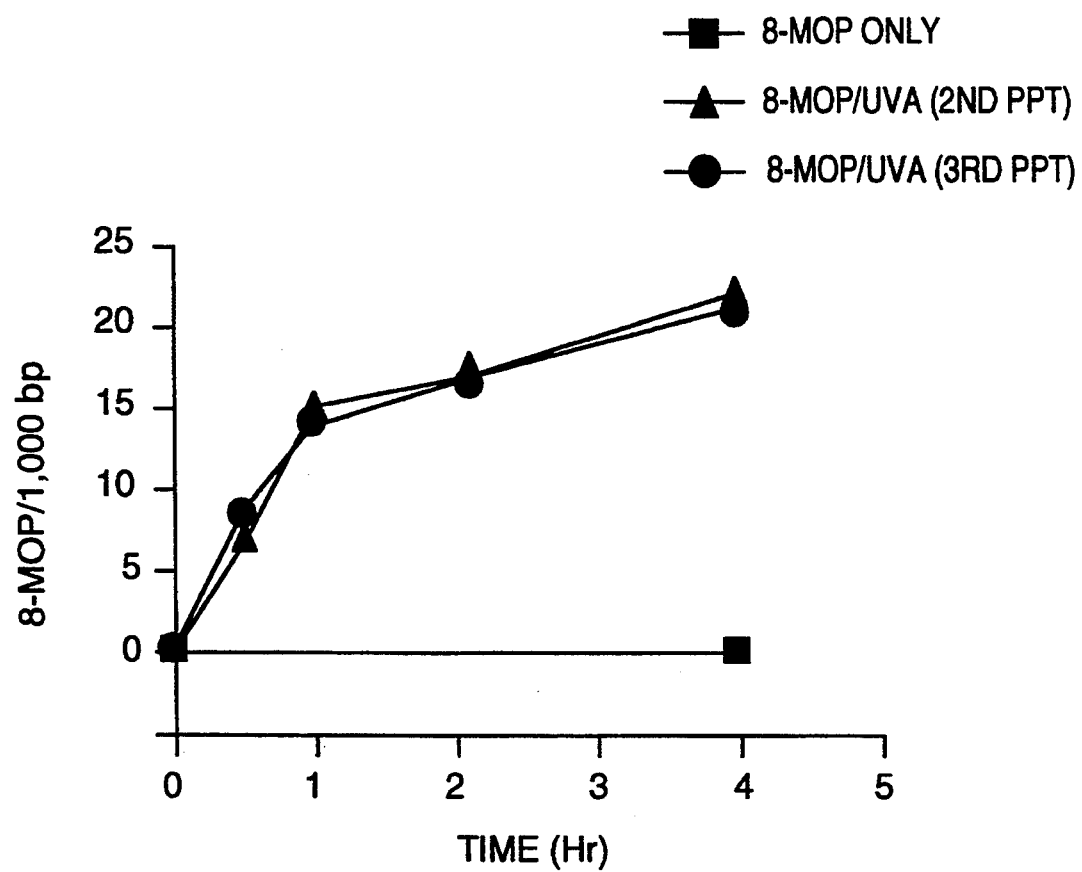
FIG. 3 is a graph showing the photoaddition of 8-methoxypsoralen to uninfected H9 cell DNA.

As shown in FIG. 3, the extent of 8-MOP photomodification of cellular DNA was a function of the time of UVA irradiation. The 8-MOP addition to cellular DNA was UVA dependent since no 8-MOP adducts were formed after 4 hours of incubation in the dark.

The same DNA samples prepared for the determination of 8-MOP photoadduct levels as described above were used for the PCR analysis. One $\mu$g (containing 3×10$^5$ copies of the HLA-DQ$\alpha$ sequence) of each DNA preparation was used per 100 $\mu$l of a PCR reaction. Each PCR reaction contains in 100 $\mu$l: 10 mM Tris-buffer pH 8.4, 50 mM KCl, 2.5 mM $MgCl_2$, 0.02% gelatin, 200 $\mu$M each of dATP, dCTP, dGTP and dTTP, 20 $\mu$Ci of $\alpha$-$^{32}$P-dCTP (3000 Ci/mmole), 50 pmoles of the upstream primer GH26, 50 pmoles of the downstream primer GH27 and 2.5 units of Taq polymerase. The DNA was amplified using the thermal profile: 95° C. for 30″, 55° C. fir 30″, and 72° C. for 1′. Samples of 20 μl each were withdrawn for analysis after 20, 25 and 30 cycles of PCR. The amplified products were separated from the unincorporated $\alpha$-$^{32}$P-dCTP by polyacrylamide gel electrophoresis (PAGE) through a 12.5% denaturing gel containing 8M urea and visualized by autoradiography.

Figure 4:
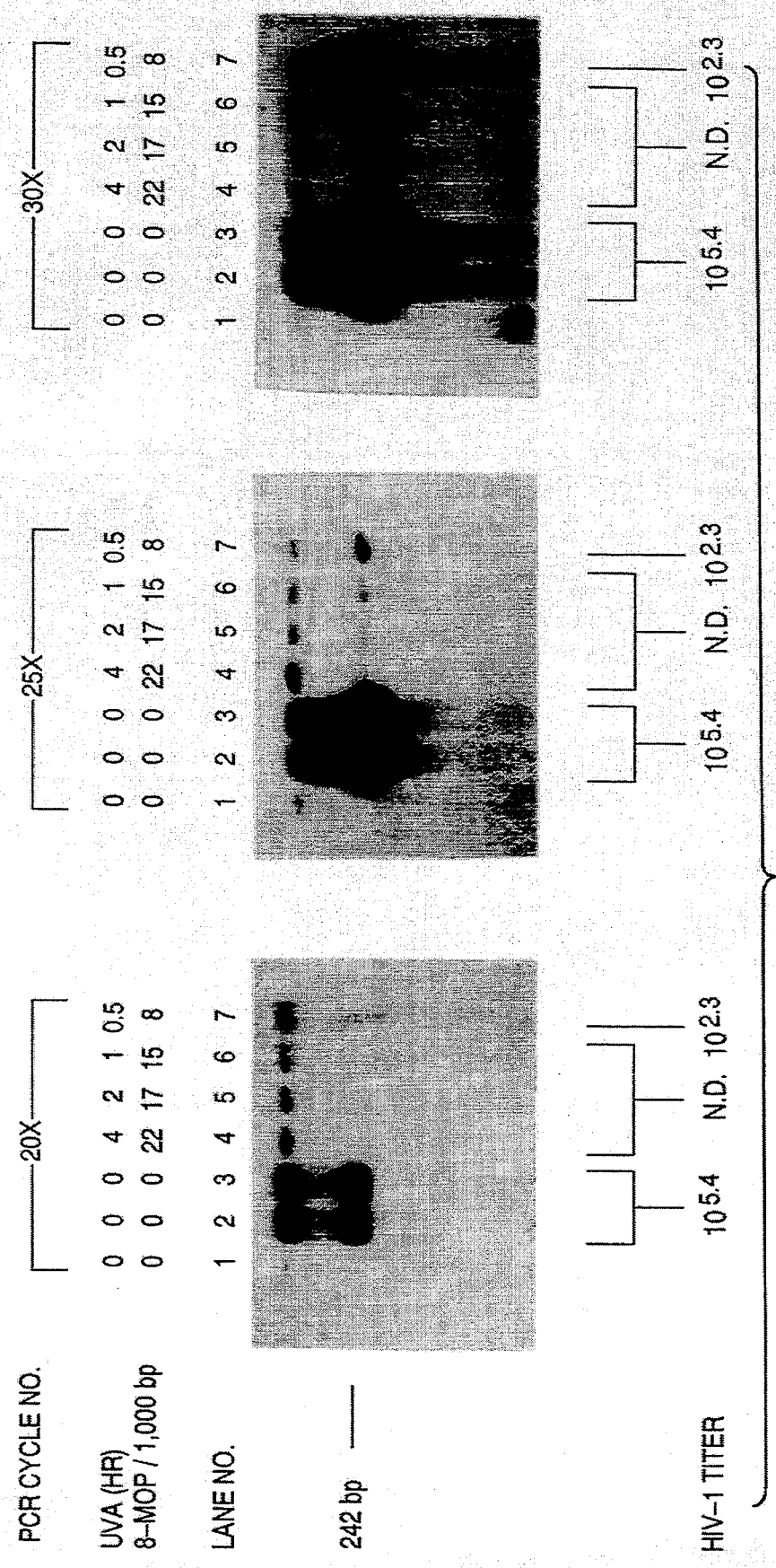
FIG. 4 is a photograph of an autoradiograph of electrophoresed, PCR-amplified, internally-radiolabelled, HLA sequences following photochemical decontamination of platelet concentrates containing uninfected H9 cells.

The results (FIG. 4) indicate that 8-MOP photoadducts on H9 cellular DNA inhibit amplification of HLA sequences. The extent of inhibition is a function of the number of adducts formed. The amplification reaction proceeded normally with the untreated DNA sample (lane 2) and the 4 hour 8-MOP (no UVA) treated DNA sample (lane 3), since neither of these samples contained 8-MOP photoadducts. By contrast, the level of amplification was drastically reduced in samples containing 8-MOP photomodification of the DNA (lanes 4-7). No amplification was present after 20 cycles when greater than 8 adducts per 1,000 bp were formed. At 25 cycles, the intensity gradient of amplified products correlated with the number of 8-MOP adducts on the DNA. At 30 cycles the PCR inhibition is still clearly evident.

Bands were excised from the gel and radioactivity was determined by scintillation counting. The amplification efficiency expressed as the relative PCR signal for 25 and 30 PCR cycles was determined from the ratio of the radioactivity of the amplicon bands (Table 2). It is clear that higher levels of photomodification resulted in a higher degree of PCR inhibition. The amplification efficiency was not determined for the 20 cycle-PCR because no amplicon bands were detected for the modified DNA.

TABLE 2

Comparison of the Relative PCR Amplification Signal of 8-MOP/UVA Treated Cellular DNA With Untreated Control DNA.

| Sample | Treatment | UVA (hr) | 8-MOP per 1,000 bp | Relative PCR Signal 25X | 30X |
|---|---|---|---|---|---|
| 1 | Reagent Only | 0 | 0 | 0 | 0 |
| 2 | Control | 0 | 0 | 100 | 100 |
| 3 | 8-MOP only | 0 | 0 | 100 | 100 |
| 4 | 8-MOP/UVA | 4 | 22 | 0.34 | 2.3 |
| 5 | 8-MOP/UVA | 2 | 17 | 0.51 | 3.2 |
| 6 | 8-MOP/UVA | 1 | 15 | 0.84 | 5.1 |
| 7 | 8-MOP/UVA | 0.5 | 8 | 1.76 | 10.8 |

At a level greater than 8 adducts/1,000 bp, no amplification product was detected after 20 cycles of PCR. After 25 cycles of PCR, the amplification product of modified DNA was detected at the level of 0.34-1.76% Of the control unmodified cellular DNA. The 1.76% level of detection corresponds to the 0.5 hour UVA irradiation, at which point 2.7 logs of HIV-1 was inactivated (see FIG. 5 and accompanying discussion below). While 0.84% amplification was detected after 1 hour of irradiation, the HIV-1 activity was undetectable by the microplaque assay (FIG. 5). These results indicate that PCR is a surrogate test which can measure the extent of inactivating modifications with more sensitivity than the biological assays. The use of increased number of PCR cycles permits quantitation of the effects of the inactivation treatment over a range where such effects may only be inferred by extrapolation when infectivity data alone are used.

EXAMPLE 4

Having established the photoaddition kinetics of 8-MOP to cellular DNA of uninfected H9 cells, this experiment establishes the inactivation kinetics of HIV-1 using infected H9 cells. Infected ($2.5 \times 10^7$) H9 cells in one ml of Dulbecco's modified Eagle's minimum essential medium (DMEM)/15% fetal bovine serum (FBS) were added to one unit of platelet concentrate. Stock 8-MOP (100 mg/ml in DMSO) was added to a final concentration of 300 μg/ml. 5 ml of the mixture was transferred to a siliconized glass chamber equipped with an outer jacket in which H$_2$O was circulated to maintain the temperature at 25° C. The gas phase above the platelet suspension was flushed with 95% N/5% Co$_2$ for 30 minutes in order to reduce the concentration of O$_2$ in the platelet concentrate and then tightly capped before placing in the irradiation device (described above). Individual samples in separate chambers were set up for each UVA irradiation time point. The control samples included an untreated sample and a sample to which only 8-MOP was added. The HIV-1 infectivity for each sample was measuring using the microplaque assay described by C. V. Hanson et al. for quantitating HIV. See J. Clin. Microbiol. 23:2030 (1990).

Figure 5A:
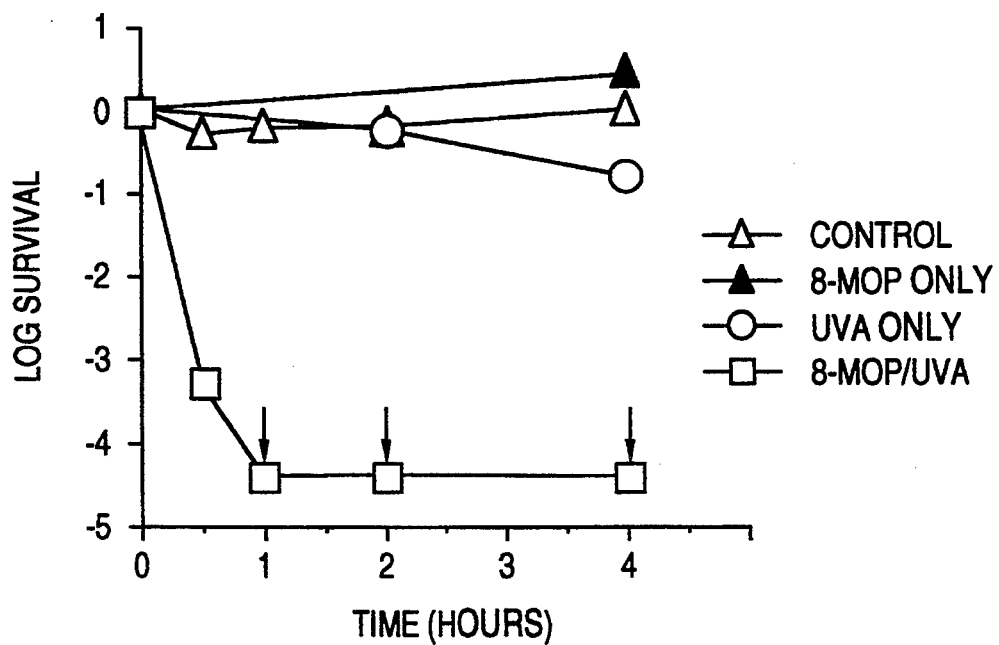
FIGS. 5A and 5B graphically shows the correlation of the biological inactivation of HIV-1 (i.e., an RNA virus) with photoaddition of 8-methoxypsoralen to viral RNA.

As seen in FIG. 5A, HIV-1 was inactivated in platelet concentrates at a rate of 4 to 5 logs/hr under the 8-MOP/UVA treatment conditions used. The viral inactivation was clearly due to the photochemical treatment since no HIV-1 inactivation was detected if either 8-MOP or UVA was used alone. After one or more hours of 8-MOP/UVA treatment, HIV activity was below the level of detectability by the plaque assay (indicated by the arrows).

In a parallel experiment (FIG. 5B), samples were irradiated for shorter time periods. A log-linear inactivation rate was obtained.

The experimental limitations do not allow measurements of greater than 4 logs of titer loss, which occurs within the first 60 minutes of exposure to 8-MOP. The important question is how to extrapolate further at the longer time points. The DNA binding data show that adducts are continually being formed out to at least 4 hrs (FIG. 3). How does the DNA binding data correlate with viral inactivation and how should it be used to estimate killing in the inactivation region for which direct measurements are not available? It should be kept in mind that the genomic targets are completely different (double-stranded DNA vs. encapsulated RNA in viral particles). One would expect that the binding by 8-MOP (which strongly prefers a double-stranded helical region) will be substantially less with the viral RNA target compared with nuclear DNA.

It is possible to relate the DNA data to RNA modifications by making the assumption that a single adduct per infectious RNA molecule/virus particle is sufficient to inactivate virus. With this assumption, the number of RNA adducts can be indirectly calculated from the inactivation data via Poisson statistics:

Inactivated fraction = $10^{-\log survival} = e^{-a}$, where a equals the average number of adducts per infectious HIV RNA molecule.

Figure 5B:
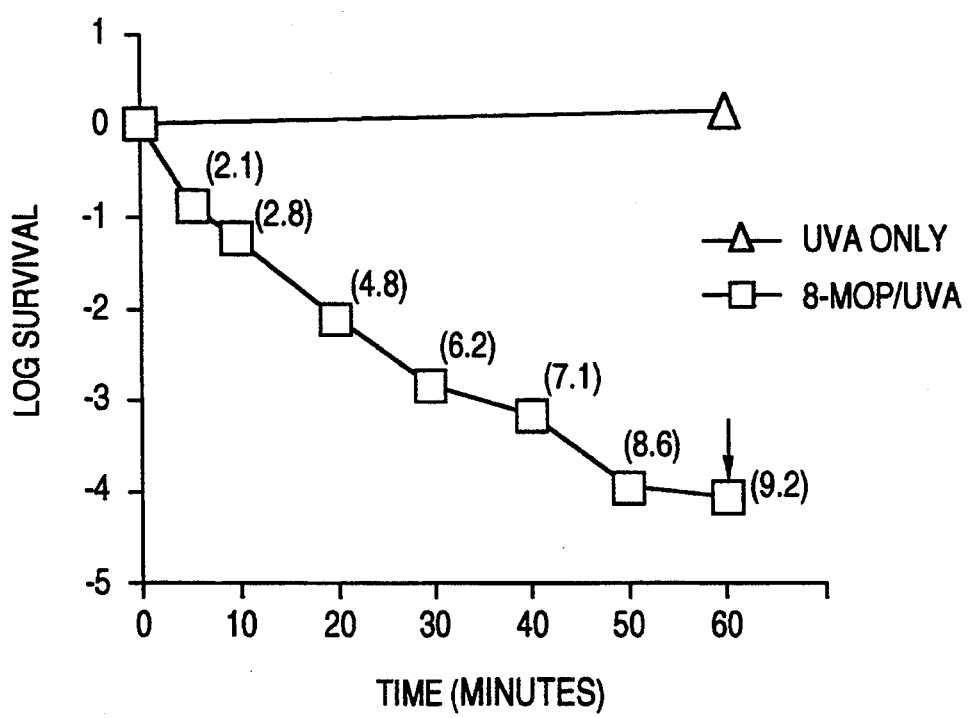

Based upon the experimental data, the range of adducts per infectious RNA molecule is 2.07 adducts at 5 minutes to 9.2 adducts at the 1 hour time point. This data is shown in FIG. 5B. The comparative data (FIG. 3 versus FIG. 5B) verifies expectations that RNA binding is substantially less than the DNA binding. 9.2 adducts per RNA genome (10,000 bases) may be equivalent to 18.4 adducts per 10,000 base pairs or 1.84 adducts per 1,000 bp. At the equivalent time point the DNA binding data yields 14 DNA adducts per 1,000 bp's, corresponding to a 7.6 fold difference in relative reactivity.

If one assumes that the differential DNA/RNA reactivity is constant over time, one can calculate the log of survival at the longer time points from the DNA data. At 4 hours, there are 22 DNA adducts. Using the 7.6 fold difference in relative reactivity, this corresponds to 14.5 adducts per RNA genome. At this average modification density per RNA genome, the frequency of an HIV RNA genome without a single 8-MOP adduct is $e^{-14.5} = 5 \times 10^{-7}$. Seven logs of inactivation is well beyond the measurement capabilities of current HIV biological assays.

To consider whether the PCR data provides a good check for the modification numbers via a "biological" measurement, one may use the experimentally obtained number of 90,000 CPM at 25 cycles of amplification of the HLA amplification of the 242mer vs. 300 CPM for the 8-MOP, 4 hour-irradiated samples (22 adducts per 1,000 bp's by $^3$H counts). From the above data and assuming that the PCR did not plateau, there is a 300 fold inactivation of this PCR sequence. The average number of adducts per amplification unit to account for this inactivation is related as:

$1/300 = e^{-a}$, which yields an average of 5.7 adducts per 242-mer.

This average number of adducts from the PCR data is extremely close to that measured by the tritium incorporation assay:

5.7 adducts/242 base pairs = 23.5 adducts per 1,000 bp's.

Thus, the relative reduction in PCR signal corresponds to the level of 8-MOP addition to cellular DNA.

EXAMPLE 5

Having established the inactivation kinetics of HIV-1, it is now possible to demonstrate the method of the present invention for measuring inactivation. A preferred embodiment of the present invention contemplates employing three different primer sets in conjunction with the PCD process: the first generating a product of a length short enough to be essentially transparent to the PCD process, the second generating a product of a length long enough to be affected—but not completely inhibited—by the PCD process, and the third generating a product of a length long enough to be completely inhibited by the PCD process (i.e., covalent addition of photoreactive compounds will be reflected by the complete absence of measurable PCR product).

Uninfected ($2.5 \times 10^7$) H9 cells in one ml of Dulbecco's modified Eagle's minimum essential medium (DMEM)/15% fetal bovine serum (FBS) were added to one unit of platelet concentrate. Stock 8-MOP (100 mg/ml in DMSO) was added to a final concentration of 300 μg/ml. 3H-8-MOP was added to a specific activity of 118 mCi/mmole. 5 ml of the mixture was transferred to a siliconized glass chamber equipped with an outer jacket in which $H_2O$ was circulated to maintain the temperature at 25° C. The gas phase above the platelet suspension was flushed with 95% $N_2$/5% $CO_2$ for 30 minutes in order to reduce the concentration of $O_2$ in the platelet concentrate and then tightly capped before placing in the irradiation device (described above). Individual samples in separate chambers were set up for each UVA irradiation time point. The control samples included an untreated sample and a sample to which only 8-MOP was added.

H9 cells were recovered from the platelet concentrate by centrifugation. The total DNA was purified using the standard phenol/chloroform extraction procedure following proteinase K digestion. Samples were prepared for PCR. One μg (containing $3 \times 10^5$ copies of the HLA-DQα sequence) of each DNA preparation was used per 100 μl of a PCR reaction. Each PCR reaction contains in 100 μl: 10 mM Tris-buffer pH 8.4, 50 mM KCl, 2.5 mM $MgCl_2$, 0.02% gelatin, 200 μM each of dATP, dCTP, dGTP and dTTP, 20 μCi of $\alpha-^{32}$P-dCTP (3000 Ci/mmole), 50 pmoles of the upstream primer, and 50 pmoles of the downstream primer and 2.5 units of Taq polymerase.

Three primer sets were used: RS40/RS80, GH26/GH27 and KM38/RS118. The amplified products were separated from the unincorporated $\alpha-^{32}$P-dCTP by electrophoresis through denaturing PAGE with the percentage of polyacrylimide specific for each amplicon:

6% gel for RS40/RS80 (989 bp amplicon)
10% gel for GH26/GH27 (242 bp amplicon)
12.5% gel for KM38/RS118 (135 bp amplicon)

Figure 6A:
FIGS. 6A, B and C are photographs of an autoradiograph of electrophoresed, PCR-amplified, internally-radiolabelled, sequences from three primer pairs following photochemical decontamination of platelet concentrates containing HIV-1 uninfected H9 cells.
Figure 6B:
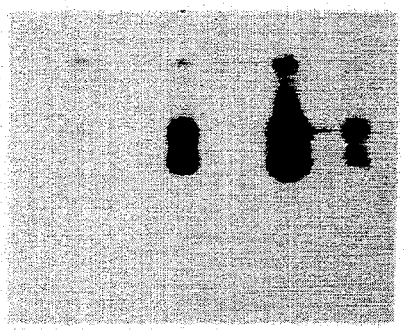
Figure 6C:

The results were visualized by autoradiography (FIG. 6). Using primer sets that are far from each other, e.g., RS40/RS80 for a 989 bp amplicon, there are enough 8-MOP adducts to "completely" inhibit PCR even after 30 cycles. Therefore, they can be used as an internal negative control (FIG. 6A). Using primer sets that are very close to each other, e.g., HM38/RS118 for the 135 bp amplicon, there will not be enough 8-MOP adducts to inhibit PCR (i.e., it is transparent to photoaddition), therefore they can be used as an internal positive control (FIG. 6C). Most importantly, with the HLA DQα primer set (FIG. 6B), a high degree of PCR inhibition is evident, demonstrating the efficacy of the PCD treatment.

For quantitation, the visualized bands were cut from the gels and collected for scintillation counting. Tables 3–5 correspond to FIGS. 6A, 6B and 6C, respectively. The raw CPM are shown for band in each gel lane. The number of PCR cycles is also indicated with the adducts per 1,000 base pair indicated in parenthesis. The Normalized Value is also given.

TABLE 3

Relative PCR Amplification Signal from primer pair RS40/RS80.

| Lane | Treatment | CPM/band | Normalized Value |
|------|-----------|----------|------------------|
| 1 | Neg. Control | 316 | — |
| 2 | 20X (0) | 4,766 | — |
| 3 | 20X (22) | 236 | — |
| 4 | 20X (8) | 440 | — |
| 5 | 25X (0) | 15,125 | 100 |
| 6 | 25X (22) | 558 | 1.6 |
| 7 | 25X (8) | 526 | 1.4 |
| 8 | 30X (0) | 31,294 | 100 |
| 9 | 30X (22) | 494 | 0.6 |
| 10 | 30X (8) | 686 | 1.2 |

TABLE 4

Relative PCR Amplification Signal from primer pair GH26/GH27.

| Lane | Treatment | CPM/band | Normalized Value |
|------|-----------|----------|------------------|
| 1 | Neg. Control | 252 | — |
| 2 | 20X (0) | 1,286 | — |
| 3 | 20X (22) | 270 | — |
| 4 | 20X (8) | 294 | — |

TABLE 4-continued

Relative PCR Amplification Signal from primer pair GH26/GH27.

| Lane | Treatment | CPM/band | Normalized Value |
|------|-----------|----------|------------------|
| 5    | 25X (0)   | 9,510    | 100              |
| 6    | 25X (22)  | 270      | 0.2              |
| 7    | 25X (8)   | 458      | 2.2              |
| 8    | 30X (0)   | 37,252   | 100              |
| 9    | 30X (22)  | 1,010    | 2.0              |
| 10   | 30X (8)   | 3,682    | 9.3              |

TABLE 5

Relative PCR Amplification Signal from primer pair KM38/RS118.

| Lane | Treatment     | CPM/band | Normalized Value |
|------|---------------|----------|------------------|
| 1    | Neg. Control  | 339      | —                |
| 2    | 20X (0)       | 2,768    | —                |
| 3    | 20X (22)      | 468      | —                |
| 4    | 20X (8)       | 532      | —                |
| 5    | 25X (0)       | 35,372   | 100              |
| 6    | 25X (22)      | 1,026    | 2.0              |
| 7    | 25X (8)       | 1,828    | 4.3              |
| 8    | 30X (0)       | 101,046  | 100              |
| 9    | 30X (22)      | 8,158    | 7.8              |
| 10   | 30X (8)       | 22,514   | 22.0             |

The Normalized Value is calculated using the raw CPM. For each cycle number, the CPM obtained using 8-MOP modified nucleic acid are divided by the CPM achieved in the case where unmodified nucleic acid is used. The latter case is taken at the value 100. The values at 20 cycles were not calculated, given the low raw CPM.

It is clear that the higher modification density results in fewer CPM and, consequently a lower normalized value. Thus, the normalized value can serve as a quantitative method for measuring pathogen inactivation.

EXAMPLE 6

While the present invention contemplates an embodiment involving seeding the blood product with nucleic acid, normally the amount of existing nucleic acid-containing cells in the blood product as a result of blood processing is sufficient. For this purpose, it is desirable to isolate nucleic acid from contaminating lymphocytes in the blood product.

8-MOP is added to one unit of platelet concentrate. 5 ml of the mixture is transferred to a siliconized glass chamber equipped with an outer jacket in which $H_2O$ is circulated to maintain the temperature at 25° C. The gas phase above the platelet suspension is flushed with 95% $N_2$/5% $CO_2$ for 30 minutes in order to reduce the concentration of $O_2$ in the platelet concentrate and then tightly capped before placing in the irradiation device (described above). Individual samples in separate chambers are set up for each UVA irradiation time point. The control samples included an untreated sample and a sample to which only 8-MOP was added.

Nucleic acid from lymphocytes is prepared from the platelet concentrate by centrifuging to create a white cell pellet and a supernatant. The supernatant is removed and the pellet is resuspended in ISOTON®II (Coulter Diagnostics, a division of Coulter Electronics, Inc., Hialeah, Fla., U.S.A.). Following a second centrifugation and wash, the cells are pelleted and thereafter lysed by the addition of protease K (50° C. for 1 hour). The protease is inactivated by heating at 95° C.

Aliquots of the lysate are added to standard PCR reactions and amplified with the three primer sets as in Example 5, above. The results are visualized by autoradiography to demonstrate the efficacy of the PCD treatment.

EXAMPLE 7

The assay is performed as in Example 6 except that the isopsoralen 4'-aminomethyl-4,5'-dimethylisopsoralen (AMDMIP) is substituted for the psoralen 8-MOP. AMDMIP is commercially available or can be synthesized according to the method of Baccichetti et al., U.S. Pat. No. 4,312,883, hereby incorporated by reference.

EXAMPLE 8

As noted previously, normally, the amount of existing nucleic acid-containing cells in the blood product as a result of blood processing is sufficient to measure inactivation of pathogens in blood product. Furthermore, the present invention contemplates that the nucleic acid may be mitochondrial DNA ("mtDNA") such as that found in platelets.

Because mtDNA differences among animal species are large, primers can be selected that amplify specific segments of human mtDNA. On the other hand, primers can be selected that amplify the corresponding segments of mtDNA from other species. See Kocher et al., Proc. Natl. Acad. Sci. USA 86:6196 (1989). The sequences of the seven primers follow, the letters L and H refer to the light and heavy strands, and the number refers to the position of the 3' base of the primer in the complete human mtDNA sequence:

| L14841 | (5'-AAAAAGCTTCCATCCAACATCTCAGCATGATGAAA-3') | (Seq. Id. No. 7) |
| and H15149 | (5'-AAACTGCAGCCCCTCAGAATGATATTTGTCCTCA-3') | (Seq. Id. No. 8) (cytochrome b); |
| L1091 | (5'-AAAAAGCTTCAAACTGGGATTAGATACCCCACTAT-3') | (Seq. Id. No. 9) |
| and H1478 | (5'-TGACTGCAGAGGGTGACGGGCGGTGTGT-3') | (Seq. Id. No. 10) (12S rRNA); |
| L15926 | (5'-TCAAAGCTTACACCAGTCTTGTAAACC-3'), | (Seq. Id. No. 11) |
| L16007 | (5'-CCCAAAGCTAAAATTCTAA-3'), | (Seq. Id. No. 12) |
| and H00651 | (5'-TAACTGCAGAAGGCTAGGACCAAACCT-3') | (Seq. Id. No. 13) (control region). |

The preferred primers are the last three primers above. These primers are expected not to amplify pathogen sequences.

We claim:

1. A method for measuring the inactivation of pathogens in blood products, comprising the sequential steps:
    a) providing i) a blood product comprising nucleic acid-containing blood cells and blood cells having no nucleic acid, ii) blood product containing means, iii) at least one photoreactive compound selected from the group consisting of psoralens, iv) amplification reagents, v) at least one amplification enzyme, vi) a first and a second primer set vii) a first and a second amplification reaction containing means, and viii.) a photoactivation device capable of emitting a given intensity of a spectrum of electromagnetic radiation comprising wavelengths of approximately 320 nm and greater;
    b) adding to said blood product in said blood product containing means said photoreactive compound to create a mixture;
    c) treating said mixture in said photoactivation device so that said photoreactive compound adds to said nucleic acid of said nucleic-acid containing blood cells;
    d) preparing said blood product such that said nucleic acid from said nucleic acid-containing blood cells is amplifiable nucleic acid;
    e) adding to said first amplification reaction containing means, in any order, a portion of said amplifiable nucleic acid, said amplification reagents, said amplification enzyme, and said first primer set, to create a reaction mixture;
    f) adding to said second amplification reaction containing means, in any order, a portion of said amplifiable nucleic acid, said amplification reagents, said amplification enzyme, and said second primer set, to create a reaction mixture;

g) exposing each of said first and second amplification reaction containing means to conditions sufficient such that said first primer set generates a product in said amplification reaction of a length sufficient to be essentially uninhibited by the addition of said photoreactive compounds to said nucleic acid of said nucleic-acid containing blood cell, and such that said second primer set generates a product in said amplification reaction of a length sufficient to be inhibited in part by the addition of said photoreactive compound to said nucleic acid of said nucleic-acid containing blood cell; and h) comparing the quantity of said amplification products in said first and second amplification reaction containing means.

2. The method of claim 1 wherein said blood product comprises platelets.

3. The method of claim 1 wherein said nucleic acid-containing blood cells are lymphocytes.

4. The method of claim 1 wherein said amplification reagents comprise Polymerase chain reaction reagents.

5. The method of claim 1 wherein said amplification enzyme is a thermally stable polymerase.

6. A method for measuring the inactivation of pathogens in blood products, comprising the sequential steps:
   a) providing i) a blood product comprising nucleic acid-containing blood cells and blood cells having no nucleic acid, ii) blood product containing means, iii) at least one photoreactive compound selected from the group consisting of psoralens, iv) amplification reagents, v) at least one amplification enzyme, vi) a first, a second and a third primer set vii) a first, a second and a third amplification reaction containing means, and viii) a photoactivation device capable of emitting a given intensity of a spectrum of electromagnetic radiation comprising wavelengths of approximately 320 nm and greater;
   b) adding to said blood product in said blood product containing means said photoreactive compound to create a mixture;
   c) treating said mixture in said photoactivation device so that said photoreactive compound adds to said nucleic acid of said nucleic-acid containing blood cells;
   d) preparing said blood product such that said nucleic acid from said nucleic acid-containing blood cells is amplifiable nucleic acid;
   e) adding to said first amplification reaction containing means, in any order, a portion of said amplifiable nucleic acid, said amplification reagents, said amplification enzyme, and said first primer set, to create a reaction mixture;
   f) adding to said second amplification reaction containing means, in any order, a portion of said amplifiable nucleic acid, said amplification reagents, said amplification enzyme, and said second primer set, to create a reaction mixture;
   g) adding to said third amplification reaction containing means, in any order, a portion of said amplifiable nucleic acid, said amplification reagents, said amplification enzyme, and said third primer set, to create a reaction mixture;
   h) exposing each of said first, second and third amplification reaction containing means to conditions sufficient such that said first primer set generates a product in said amplification reaction of a length sufficient to be essentially uninhibited by the addition of said photoreactive compounds to said nucleic acid of said nucleic-acid containing blood cell, such that said second primer set generates a product in said amplification reaction of a length sufficient to be inhibited in part by the addition of said photoreactive compounds to said nucleic acid of said nucleic-acid containing blood cell, and such that said third primer set generates a product in said amplification reaction of a length sufficient to be completely inhibited by the addition of said photoreactive compounds to said nucleic acid of said nucleic-acid containing blood cell; and
   i) comparing the quantity of said amplification products in said first, second and third amplification reaction containing means.

7. The method of claim 6 wherein said blood product comprises platelets.

8. The method of claim 6 wherein said nucleic acid-containing blood cells are lymphocytes.

9. The method of claim 6 wherein said amplification reagents comprise Polymerase chain reaction reagents.

10. The method of claim 6 wherein said amplification enzyme is a thermally stable polymerase.

11. A method of estimating inactivation of one or more pathogens by measuring the photomodification of endogenous nucleic acid in a blood product having blood cells that contain nucleic acid, comprising the steps:
    a) adding a psoralen which, upon photoactivation with a spectrum of electromagnetic radiation comprising wavelengths of approximately 320 nm and greater, binds covalently with nucleic acid to said blood product to photomodify at least some of said endogenous nucleic acid;
    b) treating said endogenous nucleic acid from said blood product to make it accessible to amplification reagents;
    c) adding a first portion of said endogenous nucleic acid of step (b) to a first amplification reaction containing means in the presence of a first primer set which can amplify a first target sequence if said first target sequence is unmodified;
    d) adding a second portion of said endogenous nucleic acid of step (b) to a second amplification reaction containing means in the presence of a second primer set which can amplify a second target sequence having sufficiently fewer base pairs than said first target sequence such that said second primer set can amplify said second target sequence in the presence of some photomodification of said endogenous nucleic acid;
    e) exposing each of said first and second amplification reaction containing means to conditions sufficient to provide amplification products of different lengths; and
    f) measuring the quantity of said amplification products in said first and second amplification reaction containing means to estimate inactivation of said pathogens, if any, present during step (a).

12. The method of claim 11 wherein said first target sequence consists of enough base pairs that photomodification of said endogenous nucleic acid inhibits in part the generation of amplification products by said first primer set.

13. A method of estimating inactivation of HIV virus by measuring the photomodification of endogenous nucleic acid in a blood product having blood cells that contain nucleic acid, comprising the steps:

a) adding 8-methoxytpsoralen which, upon photoactivation with a spectrum of electromagnetic radiation comprising wavelengths of approximately 320 nm and greater, binds covalently with nucleic acid to said blood product to photomodify at least some of said endogenous nucleic acid;

b) treating said endogenous nucleic acid from said blood product to make it accessible to amplification reagents;

c) adding a first portion of said endogenous nucleic acid of step (b) to a first amplification reaction containing means in the presence of a first primer set which can amplify a first target sequence if said first target sequence is unmodified;

d) adding a second portion of said endogenous nucleic acid of step (b) to a second amplification reaction containing means in the presence of a second primer set which can amplify a second target sequence having sufficiently fewer base pairs than said first target sequence such that said second primer set can amplify said second target sequence in the presence of some photomodification of said endogenous nucleic acid;

e) exposing each of said first and second amplification reaction containing means to conditions sufficient to provide amplification products of different lengths; and f) measuring the quantity of said amplification products in said first and second amplification reaction containing means to estimating inactivation of said HIV virus, if any, present during step (a).

14. The method of claim 13 wherein said first target sequence consists of enough base pairs that photomodification of said endogenous nucleic acid inhibits in part the generation of amplification products by said first primer set.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:1:

GTGCTGCAGG TGTAAACTTG TACCAG         26

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:2:

CACGGATCCG GTAGCAGCGG TAGAGTTG         28

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:3:

TGGTCTCCTT AAACCTGTCT TG         22

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:4:

ACACCATGGT GCACCTGACT         20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:5:

ATTTTCCCAC CCTTAGGCTG                                                      20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:6:

TGGTAGCTGG ATTGTAGCTG                                                      20

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:7:

AAAAGCTTC CATCCAACAT CTCAGCATGA TGAAA                                      35

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:8:

AAACTGCAGC CCCTCAGAAT GATATTTGTC CTCA                                      34

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:9:

AAAAGCTTC AAACTGGGAT TAGATACCCC ACTAT                                      35

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:10:

TGACTGCAGA GGGTGACGGG CGGTGTGT 28

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:11:

TCAAAGCTTA CACCAGTCTT GTAAACC 27

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:12:

CCCAAAGCTA AAATTCTAA 19

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: internal ( x i ) SEQUENCE DESCRIPTION: SEQ ID NO:13:

TAACTGCAGA AGGCTAGGAC CAAACCT 27